(12) United States Patent
Sun et al.

(10) Patent No.: US 6,768,312 B2
(45) Date of Patent: Jul. 27, 2004

(54) STRUCTURAL INTEGRITY MONITORING SYSTEM INCLUDING WIRELESS ELECTROMECHANICAL IMPEDANCE MEASUREMENT

(75) Inventors: Fanping Sun, Glastonbury, CT (US); Balkrishna S. Annigeri, Glastonbury, CT (US); Howard Winston, Woodbury, CT (US)

(73) Assignee: United Technologies Corporation, Hartford, CT (US)

( * ) Notice: Subject to any disclaimer, the term of this patent is extended or adjusted under 35 U.S.C. 154(b) by 0 days.

(21) Appl. No.: 09/875,597

(22) Filed: Jun. 6, 2001

(65) Prior Publication Data

US 2002/0190723 A1 Dec. 19, 2002

(51) Int. Cl.[7] .......................... G01R 31/08; G01R 27/02
(52) U.S. Cl. ...................................... 324/525; 324/509
(58) Field of Search ............................... 324/525, 76.12, 324/76.27, 76.28, 76.29, 76.44, 76.45, 76.49, 609; 340/870.3; 361/65; 310/311, 321

(56) References Cited

U.S. PATENT DOCUMENTS

| | | | | |
|---|---|---|---|---|
| 3,924,456 | A | * 12/1975 | Vahaviolos | ................... 73/587 |
| 3,926,039 | A | * 12/1975 | Zhukov et al. | ................ 73/627 |
| 4,181,024 | A | 1/1980 | Leak et al. | |
| 4,701,658 | A | 10/1987 | Ringermacher et al. | |
| 5,092,645 | A | * 3/1992 | Okada | ..................... 294/119.1 |
| 5,109,700 | A | 5/1992 | Hicho | |
| 5,195,046 | A | * 3/1993 | Gerardi et al. | ................. 702/35 |
| 5,349,857 | A | * 9/1994 | Kasanami et al. | ....... 73/504.14 |
| 5,383,133 | A | 1/1995 | Staple | |
| 5,817,944 | A | * 10/1998 | Chung | ........................ 73/763 |
| 5,852,793 | A | 12/1998 | Board et al. | |
| 6,076,405 | A | 6/2000 | Schoess | |
| 6,176,136 | B1 | 1/2001 | Zoppitelli et al. | |
| 6,196,062 | B1 | * 3/2001 | Wright et al. | ................ 324/210 |
| 6,246,287 | B1 | * 6/2001 | Yamashita | ................... 330/174 |
| 6,370,964 | B1 | * 4/2002 | Chang et al. | .......... 73/862.046 |

OTHER PUBLICATIONS

Paper No. 2443–29, SPIE 1995 North American Conference on Smart Structures and Materials, San Diego, CA, Feb. 26–Mar. 3, 1995, entitled "Local–area health monitoring of aircra ft via piezoelectric actuator/sensor patches," by Z. Chaudhry, T. Joseph, F. Sun, C. Rogers.

SPIE vol. 3044, article entitled "Active Damage Interrogation System for Structural Health Monitoring" by Peter F. Lichtenwalner, James P. Dunne, Ronald S. Becker and Erwin W. Baumann.

Maintenance, Repair & Overall, article entitled "Inspection Methods 'Key' to Aging Aircraft Safety," by Edward H. Phillips/Dallas.

* cited by examiner

*Primary Examiner*—N. Le
*Assistant Examiner*—John Teresinski
(74) *Attorney, Agent, or Firm*—Carlson, Gaskey & Olds

(57) ABSTRACT

A structural integrity monitoring system includes a piezoelectric sensor that is adapted to be secured to or embedded within an item of interest. A resistive element is placed in series with the piezoelectric sensor. An output from the series combination of the resistive element and the sensor is conditioned and then transmitted wirelessly to a remote location. An interface located at the remote location receives the transmitted signal, determines the content of the signal and provides an output indicative of the structural integrity of the item of interest.

24 Claims, 2 Drawing Sheets

STRUCTURAL INTEGRITY MONITORING SYSTEM INCLUDING WIRELESS ELECTROMECHANICAL IMPEDANCE MEASUREMENT

BACKGROUND OF THE INVENTION

This invention generally relates to a system for monitoring the structural integrity of an item. More particularly, this invention relates to a system for obtaining electromechanical impedance information to determine structural integrity of a chosen item.

Structural health monitoring is important in various industries. One example is the aerospace industry where mechanical flaws or the signs of upcoming mechanical flaws are important to locate and address. One hindrance to effectively conducting such monitoring on an ongoing or regular basis is the relatively expensive equipment and cumbersome procedures that are currently required.

One advance in this area has been the implementation of lead zirconate titanate (PZT) piezoelectric sensors that provide information regarding the item's structural mechanical impedance spectra. As known in the art, measuring the frequency impedance spectra using PZT sensors requires the sensor to be secured to or embedded within the item of interest. A major difficulty is presented by the need to communicate information from the sensor to a diagnostic tool that provides an output meaningful to a technician or other professional who is monitoring the structural condition of the item. Physical connections between the sensor and other equipment have always been required.

Such physical connections make the use of such sensors of limited value in many circumstances. For example, a gas turbine engine has many moving parts and many sensors would be required for an effective monitoring arrangement. Introducing multiple sensors, however, included the need to introduce multiple hardwired connections or other physical connections to other devices within the system This is impractical given the nature of a turbine engine, for example. Not only is the task cumbersome or impossible, but it proves to be overly expensive, susceptible to hardwired connection failures and renders the use of such sensors impractical under many circumstances.

There is a need for an effective structural integrity monitoring system that can utilize the information gathered with piezoelectric sensors. This invention addresses that need and avoids the shortcomings and drawbacks of the currently proposed or implemented arrangements.

SUMMARY OF THE INVENTION

In general terms, this invention is a system for monitoring the structural integrity of an item. A piezoelectric sensor is supported on the item of interest. A resistive element is coupled in series with the piezoelectric sensor. A signal conditioner conditions a signal that has a component that is indicative of a voltage drop across the piezoelectric sensor. The series connection of the sensor and the resistive element provide the ability to derive such information in a reliable manner. A transmitter transmits the conditioned signal to a remote location, preferably using wireless communication. At the remote location, an interface receives the transmitted signal and provides an indication of the structural integrity of the item based upon the information within the transmitted signal.

In one example, the piezoelectric sensor is a PZT sensor that is bonded to the item of interest. A sine wave generator preferably provides the voltage that is applied across the series connection of the resistive element and the piezoelectric sensor. The transmitter and interface device preferably communicate utilizing radio frequency signals.

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
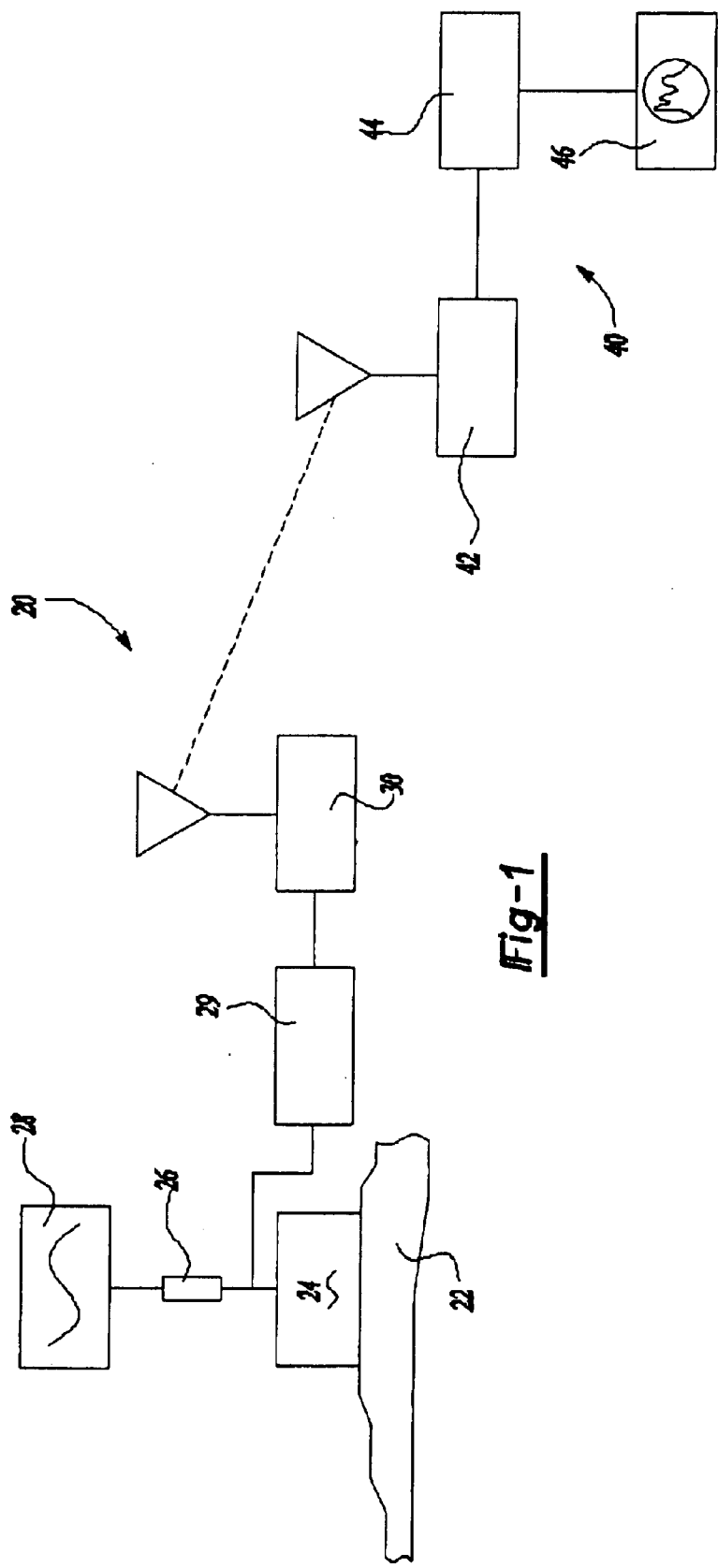
FIG. 1 schematically illustrates a system designed according to this invention.

A structural integrity monitoring system 20 provides information regarding the structural integrity or composition of an item 22 of interest. The item 22 may be a component in any one of a variety of situations. Examples include aircraft components.

A piezoelectric sensor 24 preferably is supported on the item 22 by being secured to the item or at least partially embedded within the item. In one example, the piezoelectric sensor 24 is bonded to the item 22 in a conventional manner. The preferred embodiment includes a lead zirconate titanate (PZT) piezoelectric sensor.

A resistive element 26 is coupled in series with the sensor 24. The resistive element 26 preferably has no inductance. A signal generator 28 applies a voltage across the series combination of the sensor 24 and the resistive element 26. In one example, the signal generator 28 is a sine sweep generator.

With this invention, sensor 24 acts as both an actuator and a sensor that simultaneously induces and transduces vibrations within item 22. As known in current practice, an applied electric voltage causes changes in volume of the actuator 24, which then induces vibrations in the item 22. Because the sensor 24 is embedded in the item 22, these volume changes are a unique representation of the vibrational frequency response of item 22 to the excitation applied by actuator 24. These changes in sensor 24 volume lead to corresponding changes in the current passing through sensor 24. As a result, the electric current through sensor 24 and the voltage drop across the resistive element 26 are modulated by the vibration of item 22 and are representations of the vibration spectrum of item 22 as driven by the sine sweep signal generator 28.

A signal conditioner 29 obtains a signal at the coupling between the resistive element 26 and the sensor 24. The series combination of the sensor 24 and the resistive element 26 effectively operates as a voltage divider of the signal provided by the generator 28. The signal conditioner 29 obtains, therefore, a signal having a component that is indicative of a voltage drop across the sensor 24. In one example, the signal conditioner 29 is a band pass filter tuned to a selected frequency interval. The signal conditioner 29 preferably eliminates noise that would interfere with the desired components of the signal obtained from the series combination of the sensor 24 and the resistive element 26. Examples of such noise include low frequency noise generated by environmental vibration of the item 22 and high frequency EMI noise.

The output from the signal conditioner 29 preferably modulates a high frequency carrier signal at a selected frequency. In one example, the carrier signal frequency is 900 MHz. A transmitter 30 wirelessly broadcasts the signal to an interface 40 located remotely from the sensor 24.

The interface 40 preferably includes a receiver portion 42 that receives and demodulates the transmitted signal from the transmitter 30. A signal processing portion 44 and a computing portion 46 process the received signal and provide information regarding the structural condition of the item 22.

The signal processing preferably includes temperature compensation. There are known algorithms to compensate for the effect of temperature on the accuracy of measurements obtained by the inventive system. Given this description, those skilled in the art will be able to choose a suitable temperature compensation strategy.

Figure 2:
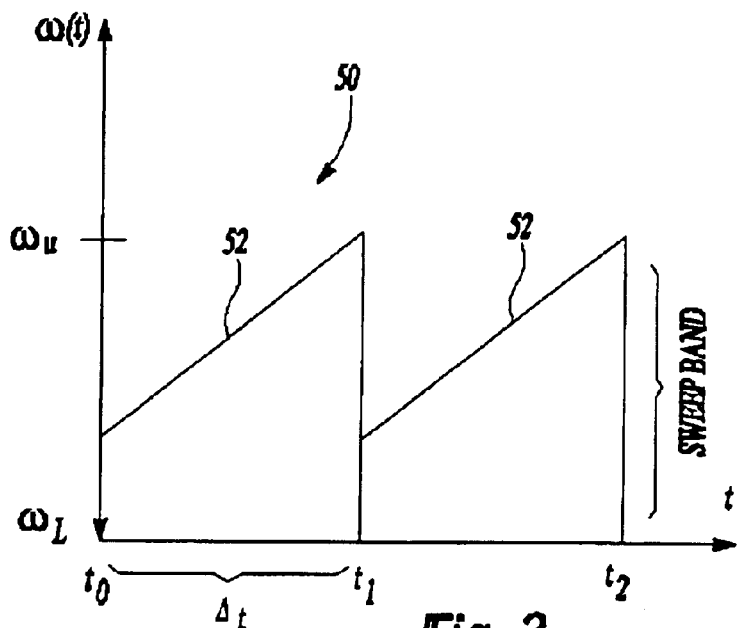
FIG. 2 is a graphical representation of an example sine sweep electric signal utilized with the embodiment of FIG. 1.

In one example, the signal generator 28 is a sine sweep generator. FIG. 2 contains a graphical plot 50 illustrating at 52 the variation in the sine wave signal from a lower frequency $\omega_l$ to an upper frequency $\omega_u$. The sinusoidal signal from the generator 28 can be represented by the following equation:

$$V_i(t) = A \cdot \sin(\omega(t) \cdot t) \quad (E1)$$

The output signal obtained by the signal conditioner 29 can be represented by the following equations:

$$V_o(t) = V_i(t) \cdot \frac{Z_{es}(\omega(t))}{Z_{es}(\omega(t)) + R} = A'(\omega(t)) \cdot \sin(\omega(t)) \cdot t) \quad (E2)$$

$$A'(\omega) = \frac{A \cdot Z_{es}(\omega)}{Z_{es}(\omega) + R}; \quad (E3)$$

where R is the DC resistance of the resistive element 26. Cracks or other types of damage in the item 22 induce corresponding changes in the item's mechanical impedance. Such changes are reflected in changes in the electromechanical impedances $Z_{es}(\omega)$ of the sensor 24 in the item 22.

The interval between the lower frequency $\omega_l$ and the upper frequency $\omega_u$ preferably is chosen to contain several mechanical resonances of the item 22. At one of the resonant frequencies, the amplitude of the output signal that is received by the signal conditioner 29 is a local maximum. Changes to the structural integrity in the item 22 cause changes in the resonant frequencies. Additionally or alternatively, significant qualitative changes in the spectrum $A'(\omega)$, such as peak splitting (e.g., as can result from damage-induced loss of symmetry of the item 22) or the disappearance of peaks, may result.

After the signal conditioner 29 has filtered the output signal containing a component indicating a voltage drop across the sensor 24, the conditioned signal is wirelessly broadcast by the transmitter 30. The signal broadcast by the transmitter can be described by the following equation:

$$V_m(t) = V_o(t) \cdot \sin(\omega_o t) \quad (E4)$$

Once received by the interface 40, the receiver 42 preferably demodulates the signal back into the original output signal $V_o(t)$ described by the above equation E2. The signal processing portion 44 preferably then transforms the output signal into a signal that represents the envelope of the output of the signal conditioner 29. This envelope signal also provides information regarding the electromechanical impedance spectrum of the sensor 24 and the item 22.

The reconstructed impedance spectrum preferably is then processed using an analog to digital channel on a computer 46 or microprocessor that is appropriately programmed for data acquisition regarding the structural condition of the item 22. Given this description, those skilled in the art will be able to appropriately program a computer to utilize the information from the obtained signal to provide an output regarding the structural condition of the item. The output of the interface 40 may be visual as illustrated in the component 46 or may be stored to computer memory, or both, depending on the needs of a given situation.

Another feature of this invention is synchronizing the signal of the signal generator 28 with data acquisition at the interface 40. In the currently preferred embodiment, the recovered impedance signature provided by the processing portion 44 is differentiated. In one example, an R-C circuit (not illustrated) differentiates the signal before it is provided to an analog to digital channel on a computer. The differentiation provides sharp pulses at times corresponding to the times $t_o$, $t_1$, and $t_2$ of FIG. 2.

Figure 3A:
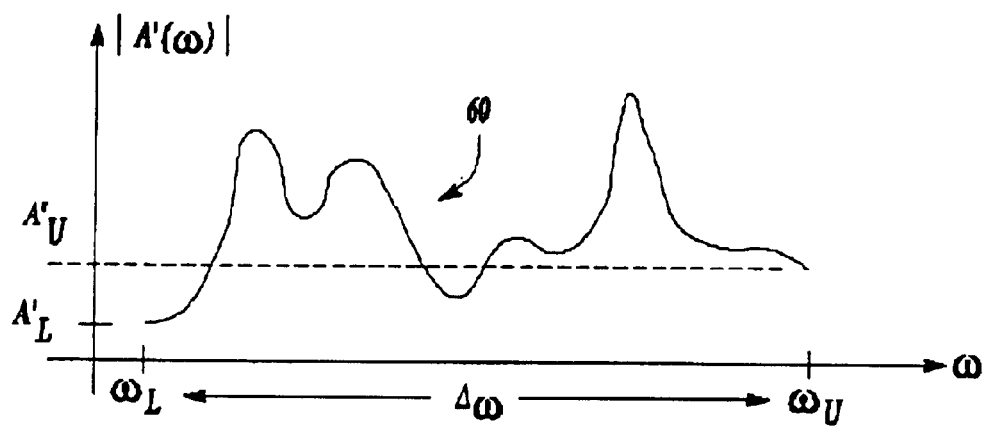
FIG. 3A is a graphical illustration of an impedance component of a signal associated with the inventive system.
Figure 3B:
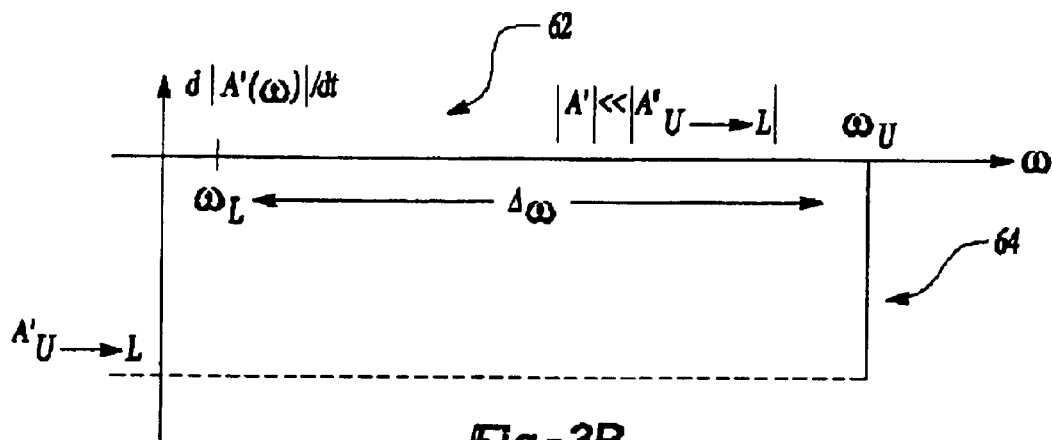
FIG. 3B graphically illustrates a differentiation of the signal illustrated in FIG. 3A.

As seen in FIG. 3A, the impedance signature 60 is a continuous and slow changing function of the frequency $\omega$. Between the various times $t_i$, the differentiated signal 62 has a relatively small value within the intervals between those discrete times. At each of the discrete times $t_i$, however, there is a step change in the sine sweep frequency $\omega$ from the lower value to the upper value and a corresponding step change in the amplitude of the impedance signature signal 60. Therefore, the result of differentiating the signal 60 at the discreet times $t_i$ provides the signal with a relatively large value at each of these instances. The arrangement of the differentiation portion of the interface 40 preferably is chosen so that the differentiated signals at the times $t_i$ are significantly larger than at any of the times between those instances. In one example, the R-C circuit is chosen to provide this result.

Within the selected sweep frequency band, the pulse of the differentiated signal uniquely identifies the start of each sweep period. An example pulse is shown at 64. Each pulse, therefore, provides synchronization information to the interface 40 regarding the operation of the signal generator 28. The interface 40 preferably is programmed to use such pulse information to synchronize data acquisition of the received signal with the operation of the signal generator 28.

This invention represents a significant improvement in the structural integrity monitoring art. The inventive system provides the ability to wirelessly transmit signals that include a representation of the impedance spectra that indicates the structural integrity of the item 22.

The preceding description is exemplary rather than limiting in nature. Variations and modifications to the disclosed embodiment may become apparent to those skilled in the art that do not necessarily depart from the purview and spirit of this invention. The scope of legal protection given to this invention can only be determined by studying the following claims.

We claim:

1. A system for determining a structural condition of an item, comprising:
   a piezoelectric sensor that is adapted to be supported on the item;
   a resistive element coupled in series with the piezoelectric sensor;

a signal conditioner that conditions a signal including an indication of a voltage drop across the sensor;

a transmitter that transmits the processed signal; and a remotely located interface that receives the transmitted signal and provides an output indicative of an impedance based upon the processed signal and the structural condition of the item.

2. The system of claim 1, wherein the resistive element has no inductance.

3. The system of claim 1, wherein the signal conditioner includes a bandpass filter.

4. The system of claim 3, wherein the bandpass filter removes signal components below approximately 50 KHz and above approximately 200 KHz.

5. The system of claim 1, wherein the transmitter and the remotely located interface communicate using wireless signal transmission.

6. The system of claim 5, wherein the transmitter and the remotely located interface utilize radio frequency signal communication.

7. The system of claim 1, wherein the interface includes a portion that determines a mechanical impedance value based upon the processed signal and determines an indication of the structural condition from the impedance value.

8. The system of claim 1, including a varying voltage generator that applies a voltage across the resistive element and the sensor.

9. The system of claim 8, wherein the voltage generator is a sine sweep generator.

10. The system of claim 1, including a differentiating portion that differentiates an impedance value based upon the transmitted signal over time and wherein the interface synchronizes data acquisition from the transmitted signal with at least one selected value of the voltage generator.

11. The system of claim 10, wherein the differentiating portion includes an RC circuit.

12. The system of claim 1, wherein the resistive element is independent of the piezoelectric sensor.

13. The system of claim 1, wherein the signal conditioned by the signal conditioner is taken from between the sensor and the resistive element.

14. A method of determining a structural condition of an item, comprising the steps of:

(a) attaching a piezoelectric sensor to the item;

(b) coupling a resistive element in series with the sensor;

(c) transmitting a signal that includes an indication of a voltage drop across the sensor to a processor located remotely from the sensor; and (d) determining a structural condition of the item from the transmitted signal.

15. The method of claim 14, including embedding the sensor within a portion of the item, using the sensor as an actuator to induce vibrations in the item and simultaneously monitoring vibration in the item using the sensor.

16. The method of claim 14, wherein step (C) includes using wireless communication.

17. The method of claim 16, wherein step (C) includes using radio frequency communication.

18. The method of claim 14, wherein step (D) includes determining an impedance value based upon the transmitted signal using the indication of the voltage drop and using the impedance value to determine the structural condition.

19. The method of claim 14 including applying a voltage with a varying frequency across the resistive element and the sensor and differentiating an impedance value based upon the transmitted signal over time to thereby determine synchronization indicators and using the indicators to synchronize data acquisition from the transmitted signal with the varying voltage.

20. The method of claim 19, including using a sine sweep generator.

21. The method of claim 14, wherein step (C) includes conditioning the signal to remove selected frequency components prior to transmitting the signal.

22. The method of claim 14, wherein the voltage drop of step (C) is frequency dependent.

23. The method of claim 14, wherein the resistive element is independent of the piezoelectric sensor.

24. The method of claim 14, including obtaining the signal of step (c) from between the sensor and the resistive element.

* * * * *